(12) United States Patent
Cann et al.

(10) Patent No.: US 9,140,669 B2
(45) Date of Patent: Sep. 22, 2015

(54) MAPPING DENSITY AND TEMPERATURE OF A CHIP, IN SITU

(71) Applicant: INTERNATIONAL BUSINESS MACHINES CORPORATION, Armonk, NY (US)

(72) Inventors: Jerome L. Cann, Jericho, VT (US); David P. Vallett, Fairfax, VT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 14 days.

(21) Appl. No.: 14/510,309

(22) Filed: Oct. 9, 2014

(65) Prior Publication Data
US 2015/0021605 A1    Jan. 22, 2015

Related U.S. Application Data (62) Division of application No. 13/669,891, filed on Nov. 6, 2012.

(51) Int. Cl.
| | | |
|---|---|---|
| *H01L 29/84* | (2006.01) | |
| *G01N 29/04* | (2006.01) | |
| *H01L 21/66* | (2006.01) | |
| *G01R 31/28* | (2006.01) | |
| *G01N 33/00* | (2006.01) | |

(52) U.S. Cl.
CPC ............ *G01N 29/04* (2013.01); *G01N 33/00* (2013.01); *G01R 31/2831* (2013.01); *H01L 22/34* (2013.01); *G01N 2033/0095* (2013.01); *G01N 2291/023* (2013.01); *G01N 2291/02818* (2013.01); *G01N 2291/02881* (2013.01); *G01N 2291/101* (2013.01)

(58) Field of Classification Search
CPC ............... G01N 2291/011; G01N 2291/0423; G01N 29/07; G01K 11/22; H01L 21/67253; H01L 22/34
See application file for complete search history.

(56) References Cited

U.S. PATENT DOCUMENTS

| | | |
|---|---|---|
| 4,106,327 A | 8/1978 | Adler et al. |
| 4,398,115 A | 8/1983 | Gagnepain et al. |
| 4,803,884 A | 2/1989 | Kaneta et al. |
| 5,136,172 A * | 8/1992 | Nakata et al. ............ 250/559.39 |

(Continued)

FOREIGN PATENT DOCUMENTS

WO    2005026668    3/2005

OTHER PUBLICATIONS

International Search Report and Written Opinion for the related PCT Application PCT/US13/55045 dated Apr. 7, 2014, 11 pages.
Luria et al. "Miniaturized CMOS Thermal Sensor Array for Temperature Gradient Measurement in Microprocessors", 2010 IEEE, pp. 1855-1858.

(Continued)

*Primary Examiner* — Jaehwan Oh
(74) *Attorney, Agent, or Firm* — Anthony Canale; Roberts, Mlotkowski, Safran & Cole, P.C.

(57) ABSTRACT

A method and system to map density and temperature of a chip, in situ, is disclosed. The method includes measuring a propagation time that a mechanical propagation wave travels along at least one predefined path in a substrate. The method further includes calculating an average substrate density and temperature along the at least one predefined path as a function of the propagation time and distance. The method further includes determining a defect or unauthorized modification in the substrate based on the average substrate density being different than a baseline substrate density.

14 Claims, 4 Drawing Sheets

(56) References Cited

U.S. PATENT DOCUMENTS

| | | | |
|---|---|---|---|
| 5,469,742 A * | 11/1995 | Lee et al. | 73/597 |
| 6,112,595 A * | 9/2000 | Stanke et al. | 73/597 |
| 6,188,050 B1 | 2/2001 | Duifer et al. | |
| 6,327,890 B1 | 12/2001 | Galipeau et al. | |
| 6,773,158 B2 | 8/2004 | Koshimizu | |
| 6,879,924 B2 * | 4/2005 | Ye et al. | 702/117 |
| 6,914,764 B2 | 7/2005 | Clabes et al. | |
| 7,397,263 B2 | 7/2008 | Condon et al. | |
| 7,434,989 B2 | 10/2008 | Solie | |
| 7,549,791 B2 | 6/2009 | Penavaire et al. | |
| 7,914,202 B2 | 3/2011 | Kamei | |
| 8,269,979 B2 | 9/2012 | Klein et al. | |
| 2005/0055171 A1 * | 3/2005 | Freund et al. | 702/89 |
| 2005/0089077 A1 | 4/2005 | Jones et al. | |
| 2009/0175313 A1 | 7/2009 | Kordic et al. | |
| 2010/0007444 A1 | 1/2010 | Nordin et al. | |
| 2010/0186513 A1 | 7/2010 | Kalinin | |
| 2011/0150031 A1 * | 6/2011 | Abdelmoneum et al. | 374/117 |

OTHER PUBLICATIONS

Yasuda "On-Chip Temperature Sensor with High Tolerance for Pocess and Temperature Variation", IBM Japan, 4 pages, 2005.

Stewart et al. "Finite Element Modeling of the Effects of Mounting Stresses on the Frequency Temperature Behavior of Surface Acoustic Wave Devices", Vectron International, 17 pages, http://www.vectron.com/products/literature_library/art3/art3.htm, 1997.

Buff et al. "Passive Remote Sensing for Temperature and Pressure Using SAW Resonator Devices", IEEE Transactions on Ultrasonics, Ferroelectrics and Frequency Control, vol. 45, Issue: 5, Publication Year: 1998, pp. 1388-1392.

Hoummady et al. "Acoustic Wave Sensors: Design, Sensing Mechanisms and Applications", Smart Mater. Struct 6, 1997, pp. 647-657.

Reindl "Wireless Passive SAW Identification Marks and Sensors", TU Clausthal, IEI, 115 pages, 2004.

Notice of Allowance dated Nov. 17, 2014 in related U.S. Appl. No. 13/669,891, 8 pages.

* cited by examiner

MAPPING DENSITY AND TEMPERATURE OF A CHIP, IN SITU

FIELD OF THE INVENTION

The invention relates to semiconductor structures and, more particularly, to methods and systems to map density and temperature of a chip, in situ.

BACKGROUND

Integrated circuit (IC) design, test, reliability, failure analysis and system design teams need the ability to monitor an IC's temperature, in situ. In addition to the average temperature of the IC, transient and/or localized hot spots also need to be detected and addressed by the IC or system. Known methods for measuring such temperature or localized hot spots include the use of one or more thermal resistors, thermal diodes, and/or digital temperature sensors incorporated directly into the IC, preferably in the active area. Other known methods include external sensors such as laser interferometers and solid state thermal imagers to record temperature remotely at each XY grid location or pixel of the IC.

The thermal resistors, thermal diodes, and/or digital temperature sensors, however, use valuable real estate of the IC, within the active areas. Also, the thermal resistors, thermal diodes, and/or digital temperature sensors may not provide accurate readings, because they may be placed far away from any temperature change and as such do not provide the ability to measure the average temperature over a specific predetermined area of the IC. For example, it is not known during the design phase where all of the transient and/or localized hot spots will occur, requiring multiple sensors be spread throughout the most active regions (and most valuable real estate) of the IC. Even then, these sensors may not be located near hot spots created by packaging or other thermal barriers (thermal resistance), or near hot spots created by electrically resistive defects that pass functional, structural, parametric and other testing.

Remote temperature sensors such as laser interferometers and solid state thermal imagers are incapable of accurately measuring the temperature of the IC at subsurface locations when one or more overlying films act to diffuse the heat. These unpredictable hot spots can lead to lower performance (lower revenue), increased test costs, increased system costs, increased operating costs, and premature failure of the IC (lower reliability, lower customer satisfaction, and lower revenue). Other drawbacks of the thermal resistors, thermal diodes, and/or digital temperature sensors include processing dependencies which require calibration in order to obtain measurement accuracies better than 2° C. to 3° C.

Accordingly, there exists a need in the art to overcome the deficiencies and limitations described hereinabove.

SUMMARY

In an aspect of the invention, a method comprises measuring a propagation time that a mechanical propagation wave travels along at least one predefined path in a substrate. The method further comprises calculating an average substrate density and temperature along the at least one predefined path as a function of the propagation time and distance. The method further comprises determining a defect or unauthorized modification in the substrate based on the average substrate density being different than a baseline substrate density.

In an aspect of the invention, a chip comprises at least one transmitter and at least one receiver, the at least one transmitter generating a mechanical wave which is received by the at least one receiver. The chip further comprises a timing circuit in communication with the at least one transmitter and the at least one receiver, which measures a time in which the mechanical wave travels between the at least one transmitter and the at least one receiver.

In an aspect of the invention, a method in a computer-aided design system for generating a functional design model of a chip, the method comprises: generating a functional representation of an active region with at least one device which generates heat; generating a functional representation of at least one transmitter and at least one receiver, the at least one transmitter generating a mechanical wave which is received by the at least one receiver; and generating a functional representation of a timing circuit in communication with the at least one transmitter and the at least one receiver, which measures a time in which the mechanical wave travels between the at least one transmitter and the at least one receiver.

In another aspect of the invention, a design structure tangibly embodied in a machine readable storage medium for designing, manufacturing, or testing an integrated circuit is provided. The design structure comprises the structures of the present invention. In further embodiments, a hardware description language (HDL) design structure encoded on a machine-readable data storage medium comprises elements that when processed in a computer-aided design system generates a machine-executable representation of the chip, which comprises the structures of the present invention. In still further embodiments, a method in a computer-aided design system is provided for generating a functional design model of the chip.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The invention relates to semiconductor structures and, more particularly, to methods and systems to map density and temperature of a chip, in situ. More specifically, the present invention relates to a method and system for acoustically mapping silicon density and temperature of an integrated circuit (IC), in situ. In embodiments, the present invention utilizes one or more Surface Acoustic Wave (SAW) Microelectromechanical system (MEMS) devices at one or more locations in an IC to provide such mapping. In embodiments, the SAW MEMS devices are preferably located at the periphery of the IC or on a dedicated 3D layer so as to not consume or interfere with the region of interest, the valuable and active areas within the IC. Although the present invention is described with the use of SAW MEMS devices, it should be understood by those of skill in the art that other types of mechanical wave transmitters and receivers are also contemplated by the present invention, e.g., bulk acoustic wave (BAW) devices.

In more specific embodiments, instead of measuring the temperature at a single point on a chip (as is done in conventional systems), it is now possible to measure/calculate an average temperature along a propagation path and over a predetermined area. It is also possible to identify hot spots on the chip, by implementing the processes of the present invention. Also, advantageously, the present invention can map the density/temperature of an IC region without embedding sensors in the active region. Moreover, the present invention is not process dependent and thus does not require calibration to compensate for process variations. It should be understood by those of skill in the art that relative baseline or other calibration may be required for other reasons.

In embodiments, the SAW MEMS (or BAW) transmitters and receivers (or transceivers) can be used to calculate the density of the substrate (e.g., silicon) and hence calculate an average temperature along a path between the transmitter and receiver integrated onto the chip. This can be accomplished by measuring a propagation time of a mechanical wave, along a path, calculating the average substrate density as a function of the time and path distance, and then calculating the average temperature as a function of the substrate density when it is within predetermined limits. For example, as travel time is a function of substrate (e.g., Si) density and the distance between transmitter and receiver along the path of travel, and density is a function of temperature, the average temperature along the path of travel can be calculated from the time it takes for a mechanical (acoustic) wave to travel a fixed and known distance from the transmitter to the receiver.

By way of further illustrative, non-limiting example, if multiple transmitters and receivers are placed around the periphery, then multiple intersecting stripes (paths) representing the average temperature of each path or a combination of paths or larger areas can be calculated. From these multiple intersecting temperature paths, a density/thermal map can be generated from which both the average temperature of the IC as well as identification of a hot spot can be made. In addition to temperature, other factors that affect substrate (e.g., Si) density can be detected and located, including void and delamination defects. These defects can be detected during manufacturing, test, in situ (during system operation) and/or failure analysis. Moreover, for counterfeit and security purposes, the in situ thermal map could be compared to a reference map to determine if the active regions within the IC match the design for a given operation.

Figure 1:
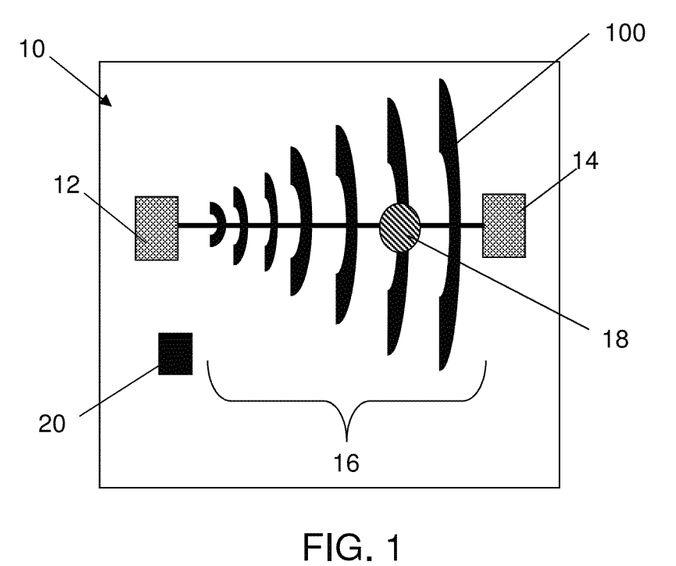
FIG. 1 shows a semiconductor structure in accordance with aspects of the present invention.

FIG. 1 shows a semiconductor structure in accordance with aspects of the present invention. More specifically, FIG. 1 shows a chip (IC) 10 with an active region 16. The active region 16 can include one or more devices that are capable of generating a localized temperature increase during use. The chip 10 further includes a transmitter 12 and a receiver 14, remote from the transmitter 12. The transmitter 12 and the receiver 14 are preferably located at a periphery of the chip 10, remote from the active region 16; although they can be provided at other locations on the chip, e.g., on a dedicated 3D layer. The transmitter 12 and the receiver 14 can be, for example, a SAW MEMS device, fabricated directly on the chip 10. In embodiments, the transmitter 12 and the receiver 14 can also be other types of mechanical wave transmitters and receivers such as bulk acoustic wave (BAW) devices. It should also be understood by those of skill in the art that the transmitter 12 and the receiver 14 can be a transceiver in any of the aspects of the present invention.

FIG. 1 further shows a timing circuit 20, which is connected (in electrical communication) to both the transmitter 12 and the receiver 14. In embodiments, the timing circuit 20 is any well known timing circuit, which can be synchronized with the transmitter 12. The synchronization between the transmitter 12 and the timing circuit 20 directs the timing circuit 20 to begin counting at the instance the mechanical propagation wave 100 is generated by the transmitter 12, e.g., T=0. The propagation time of the electrical signals for synchronization purposes is insignificant compared to the propagation time of the mechanical wave, but could easily be accounted for by those skilled in the art if necessary. In embodiments, the timing circuit 20 can trigger the transmitter 12 or vice versa, in order to ensure that the timing circuit 20 begins to count at T=0. In either scenario, the timing circuit will measure the time that the mechanical propagation wave travels across a path between the transmitter 12 and the receiver 14.

By way of illustrative example, the following baseline parameters are known: the travel time of the propagation wave between the transmitter 12 and the receiver 14 at a known distance and substrate density. As shown representatively in FIG. 1, the transmitter 12 generates a mechanical wave 100 that will propagate along a path between the transmitter 12 and the receiver 14. In operation, the transmitter 12 can be triggered by the timing circuit 14, or vice versa. The mechanical wave 100 is detected by the receiver 14, and a time of travel of the mechanical wave between the transmitter 12 and the receiver 14 is measured by the timing circuit 20. As should be understood by those of ordinary skill in the art, any hot spot (change in local temperature) 18 generated by a device in the active area 16 of the chip 10 will change the substrate density in the region of hot spot, which, in turn, will change the propagation time of a mechanical wave 100 passing through that region along the path between the transmitter 12 and the receiver 14.

From the mechanical propagation time and the fixed distance of travel between the transmitter 12 and receiver 14, it is now possible to calculate an average Si density along that path from a standard equation representing the density of the substrate, e.g., Si, as a function of time and distance. Specifically, as temperature rises, the density of the substrate (e.g., Si) will lower, which is represented by the shorter travel time of the wave along the path between the transmitter 12 and the receiver 14. Accordingly, the travel time of the propagation wave 100 and distance between transmitter and receiver is used to determine the substrate (e.g., Si) density along the path of travel. That is, it is now possible to calculate an average substrate density along the at least one predefined path as a function of the propagation time and distance. The substrate (e.g., Si) density, in turn, is used to calculate an average temperature along the path of travel, using known computations, periodic element reference tables and equations for density as a function of temperature. Thus, the propagation time can be translated into an average temperature reading, e.g., an average temperature of infinite points along the path of travel.

More specifically, a propagation time that a mechanical propagation wave 100 travels along at least one predefined path in a substrate is measured. The present invention will calculate an average substrate density along the at least one predefined path as a function of the propagation time and distance. A defect in the substrate based on the average substrate density being significantly different than a baseline substrate density is then determined. In embodiments, a defect in the substrate is determined when the average substrate density is outside a predetermined range, e.g., perhaps +/−10% from a baseline density.

In additional embodiments, the present invention can also be used to detect a failure of the chip, e.g., delamination or voids. For example, in embodiments, the failure can prevent the mechanical wave from propagating to the receiver 14 within a certain time period. As the time period exceeds the certain time period, e.g., becomes very long or even infinite, it can be inferred from such data that the chip has delaminated or formed a void. This same process can be used for any of the aspects of the present invention.

Figure 2:
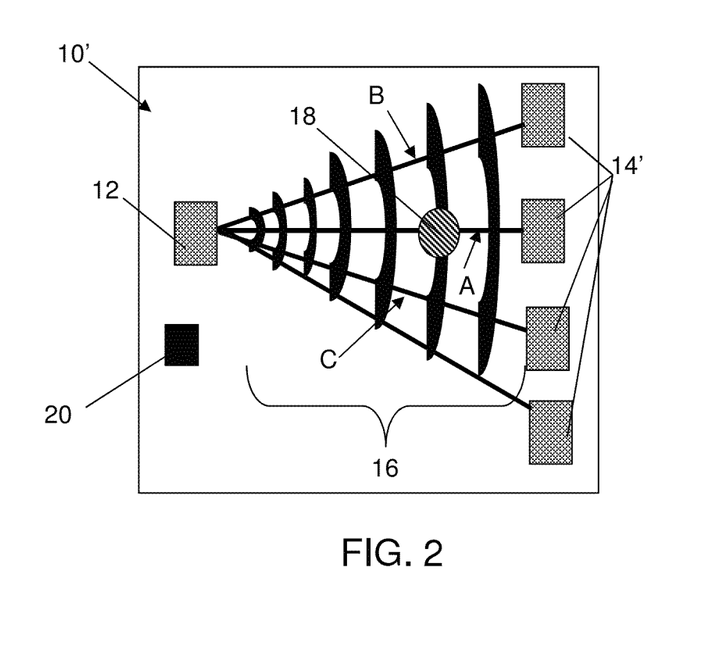
FIGS. 2-5 show respective semiconductor structures in accordance with additional aspects of the present invention.

FIG. 2 shows a semiconductor structure in accordance with additional aspects of the present invention. More specifically, FIG. 2 shows a chip (IC) 10' with an active region 16, which can include one or more devices that are capable of generating a localized temperature increase during use. The chip 10' further includes a transmitter 12 at one location and a plurality of receivers 14' at another location, remote from the transmitter 12. The transmitter 12 and the plurality of receivers 14' are preferably located at a periphery of the chip 10', remote from the active region 16; although they may also be provided at other locations, e.g., on a dedicated 3D layer. The transmitter 12 and the plurality of receivers 14' can be, for example, a SAW MEMS device; although other types of mechanical wave transmitters and receivers are also contemplated by the present invention, e.g., BAW devices. A timing circuit 20 is connected (electrically connected) to the transmitter 12 and the plurality of receivers 14 (as discussed with reference to FIG. 1.

As shown representatively in FIG. 2, the transmitter 12 generates a mechanical wave that will propagate along several paths between the transmitter 12 and the plurality of receivers 14'. In operation, the mechanical wave is detected by each of the plurality of receivers 14', along separate paths. A time of travel along each path can be measured by the timing circuit 20 and, as described above, any change in local temperature 18 in the chip 10' can be calculated by using the mechanical propagation time of the wave along any of the respective paths (due to the change in substrate (e.g., Si) density along the respective path(s)). That is, from the mechanical propagation time, as described above, it is now possible to calculate the average substrate density along the path(s), which, in turn, is used to calculate an average temperature along the respective path(s).

Advantageously, by determining a propagation time of each path between the transmitter 12 and the plurality of receivers 14', a specific location of the hot spot 18 can be identified on the chip 10'. More specifically, in implementing the processes of the present invention, it can be determined that a local temperature change occurs somewhere along path "A" due to the measured mechanical propagation time; whereas, there is no temperature change along paths "B" and "C", inferred from the fact that there is no change in mechanical propagation time in the mechanical wave. By making such determinations, it is now possible to isolate the location of the temperature change centered between the bisecting paths "B" and "C" and centered on path "A", as shown representatively in FIG. 2.

Figure 3:
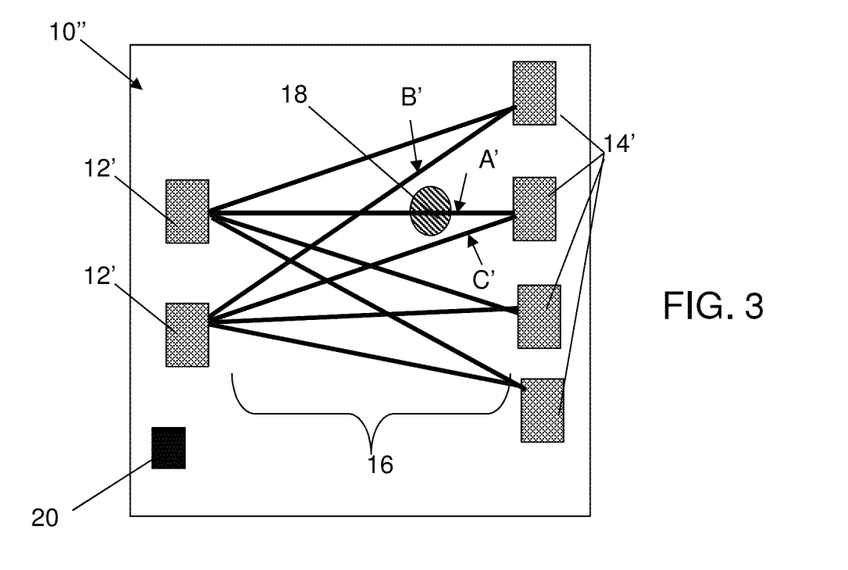

FIG. 3 shows a semiconductor structure in accordance with additional aspects of the present invention. More specifically, FIG. 3 shows a chip (IC) 10" with an active region 16, which can include one or more devices that are capable of generating a localized temperature increase during use. The chip 10" further includes two transmitters 12' and a plurality of receivers 14'. The transmitters 12' and the plurality of receivers 14' are preferably located at a periphery of the chip 10", remote from the active region 16; although they may also be provided at other locations, e.g., on a dedicated 3D layer. The transmitters 12' and the plurality of receivers 14' can be, for example, a SAW MEMS device; although other types of mechanical wave transmitters and receivers are also contemplated by the present invention, e.g., BAW devices. A timing circuit 20 is connected (in electrical communication) to each of the transmitters 12' and the receivers 14'.

As shown representatively in FIG. 3, the transmitters 12' each generate a mechanical wave that will propagate along separate paths between the transmitters 12' and each of the respective plurality of receivers 14'. In operation, a respective mechanical wave is detected by each of the plurality of receivers 14', along the separate paths. A time of travel of the wave between the transmitters 12' and each of the plurality of receivers 14' can be measured by the timing circuit 20. As described above, any change in local temperature 18 in the chip 10" will change the mechanical propagation time along the respective path(s) (due to the change in substrate density). That is, comparing the propagation time of the mechanical wave to a baseline, as described above, it is now possible to calculate the change in substrate density along a path. The change in density can then be used to calculate an average change in temperature along the respective path(s).

Advantageously, by comparing each path between the transmitters 12' and the plurality of receivers 14', a specific location of the hot spot 18 can be isolated on the chip 10". More specifically, in implementing the processes of the present invention, it can be determined that a local temperature change occurs somewhere along path "A'" due to the calculated propagation time; whereas, there is no temperature change along paths "B'" and "C'", inferred from the fact that there is no change in propagation time. By making such determinations, it is now possible to identify the location of the temperature change centered between the bisecting paths "B'" and "C'" and centered on path "A'", as shown representatively in FIG. 3. As compared to the structures shown in FIGS. 1 and 2, the resolution of the location of the temperature change can be improved due to the increased number of propagation paths.

Figure 4:
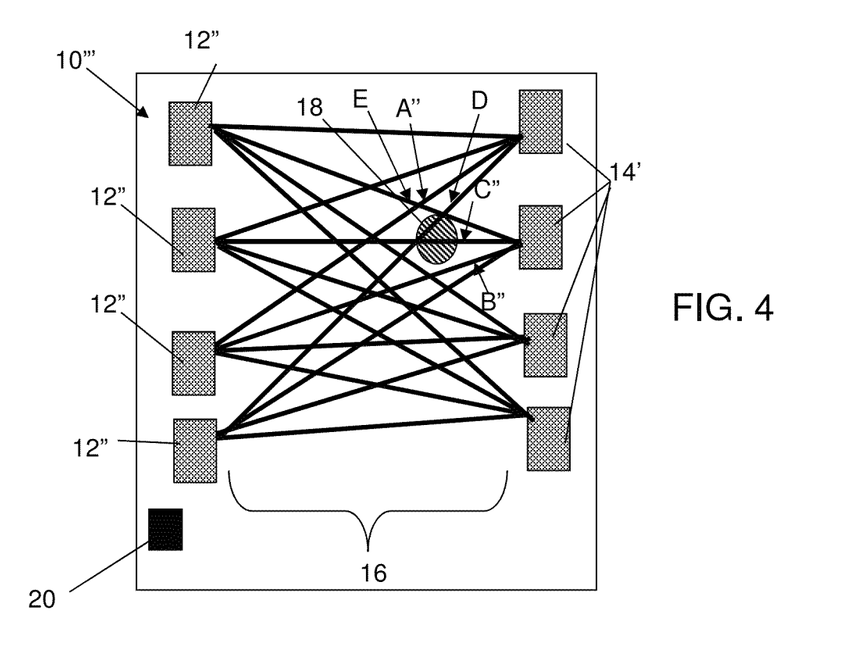

FIG. 4 shows a semiconductor structure in accordance with additional aspects of the present invention. More specifically, FIG. 4 shows a chip (IC) 10'" with an active region 16, which can include one or more devices that are capable of generating a localized temperature increase during use. The chip 10'" further includes a plurality of transmitters 12" and a plurality of receivers 14', preferably located at a periphery of the chip 10'"; although they may also be provided at other locations, e.g., on a dedicated 3D layer. The transmitters 12" and the receivers 14' can be, for example, a SAW MEMS device; although other types of mechanical wave transmitters and receivers are also contemplated by the present invention, e.g., BAW devices. A timing circuit 20 is connected (in electrical communication) to each of the transmitters 12" and the receivers 14'.

As shown representatively in FIG. 4, the transmitters 12" generate a mechanical wave that will propagate between the transmitters 12" and the respective receivers 14'. In operation, each wave is detected by each of the plurality of receivers 14', along separate paths. A time of travel of the wave between the transmitters 12" and each of the plurality of receivers 14' can be measured by the timing circuit 20, along the paths. As described above, any change in local temperature 18 in the chip 10'" will result in a change in mechanical propagation time of the wave along the respective path(s). That is, comparing the propagation time to a baseline, as described above, it is now possible to calculate the change in substrate density along a respective path. The change in density can then be used to calculate an average change in temperature along the respective path(s).

Also, as described above, by comparing each path between the transmitters 12' and the plurality of receivers 14', a specific location of the hot spot 18 can be isolated on the chip 10'''. More specifically, in FIG. 4, a temperature change occurs between bisecting paths A'', B'', C'', D and E, e.g., centered on paths C'' and D, and centered between paths A'', B'' and E. As compared to the structures shown in FIGS. 1-3, the location of the temperature change can be even more precisely located, due to the increased number of propagation paths.

Figure 5:
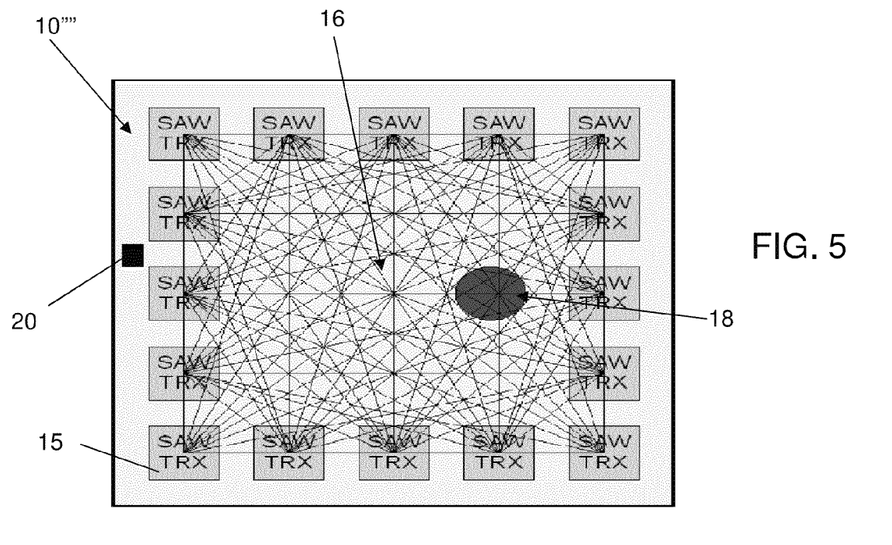

FIG. 5 shows a semiconductor structure in accordance with additional aspects of the present invention. More specifically, FIG. 5 shows a chip (IC) 10'''' with a plurality of transceivers 15 about the periphery of the chip 10''''. The transceivers 15 are preferably located around the entire periphery of the chip 10'''', remote from the active region 16; although they may also be provided at other locations, e.g., on a dedicated 3D layer. As in the other aspects of the present invention, the transceivers 15 can be, for example, a SAW MEMS device; although other types of mechanical wave transmitters and receivers are also contemplated by the present invention, e.g., BAW devices. A timing circuit 20 is connected (in electrical communication) to each of the transceivers 15.

As shown representatively in FIG. 5, the transceivers 15 can sequentially (or in some other order as with any of the aspects of the present invention) generate a mechanical wave that will propagate along individual paths between each of the transceivers 15. In operation, each wave is detected by each of the plurality of transceivers 15 along the separate paths, and a change in local temperature 18 in the chip 10'''' can be very narrowly identified, by determining which paths have a propagation delay, as measured separately (and, in embodiments, sequentially) by the timing circuit 20, as described above.

Although FIGS. 1-5 show specific configurations of the transmitters and receivers, the present invention contemplates other locations. For example, in embodiments, several receivers can be aligned with a single transmitter in order to measure a propagation time between each of the several receivers. In further embodiments, multiple transmitters can be used with a single receiver. In still additional embodiments, one of skill in the art should understand that any of the configurations can be provided around the periphery of the chip, in an active area of the chip or on different layers of the chip. In addition, one of skill in the art would understand that the local hot spots or other temperature changes can be mapped using the present invention, e.g., by identifying the hot spots as discussed with reference to FIGS. 2-5. Moreover, although the present invention was discussed with reference to an Si substrate, any substrate is contemplated to be used with the present invention. In addition, it should be understood that the SAW center-frequency ($f_o$) equals acoustic velocity/IDT (Interdigital transducer) periodicity. As an example, ZnO (acoustic coupling layer) with 1 micron IDT spacing will result in a $f_o$=6.4 GHz (6400 m/s/1 micron). By knowing the frequency, it is possible to calculate the time period that the wave can travel a known distance between the transmitter 12 and the receiver 14.

Figure 6:
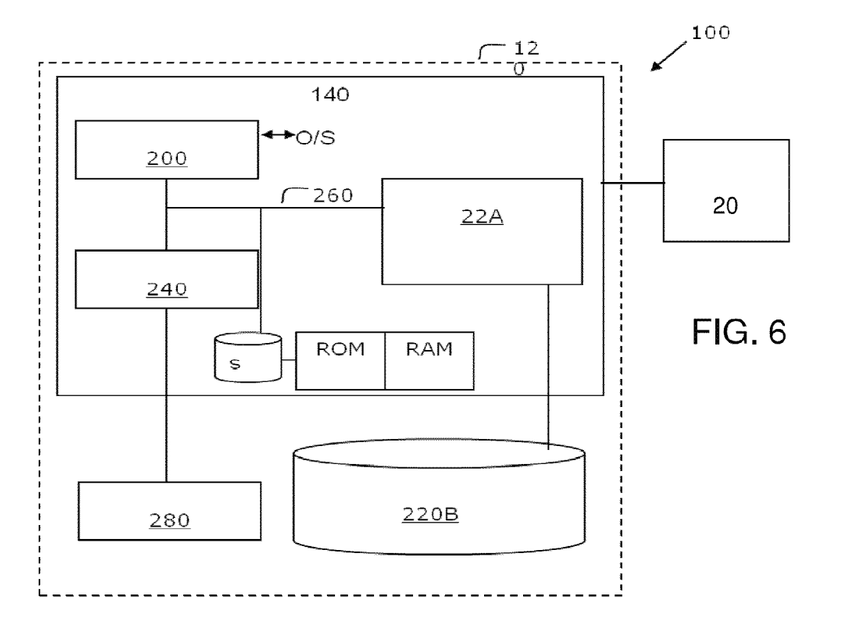
FIG. 6 shows a computing system implementing aspects of the present invention.

FIG. 6 shows an illustrative environment 100 for managing the processes in accordance with the invention. As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device "s", or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 6 shows an illustrative environment 100 for managing the processes in accordance with the invention. The environment 100 includes a computing system 12 that can perform the processes described herein. In particular, the computing system 12 includes a computing device 140, which may be connected to the timing circuit 20. The computing device 140 can be resident on a network infrastructure, or can be embedded on the chip, itself. The computing device 140 includes a processor 200, memory 22A, an I/O interface 240, and a bus 260. The bus 260 provides a communications link between each of the components in the computing device 140. In addition, the computing device includes random access memory (RAM), a read-only memory (ROM), and an operating system (O/S). The computing device 140 is in communication with the external I/O device/resource 280 and the storage system 220B. The I/O device 280 can comprise any device that enables an individual to interact with the computing device 140 and the chip 10 (e.g., timing circuit 20). The program control will provide the processes of the present invention, e.g., compare the measured time of the propagation wave along a path to the known time to determine the average temperature change along the path based on a change in substrate density, and acoustically map silicon or other substrate density and temperature of an integrated circuit (IC), in situ, etc.

It should be understood by those of skill in the art that it is possible to generate sound waves with different velocities dependent on a deformation mode. Sound waves generating volumetric deformations (compressions) and shear deformations are called longitudinal waves and shear waves, respectively. The sound velocities of these two type of waves propagating in a homogeneous 3-dimensional solid are respectively given by:

$$c_1 = \sqrt{\frac{K + \frac{4}{3}G}{\rho}} = \sqrt{\frac{Y(1-v)}{\rho(1+v)(1-2v)}}$$

$$c_2 = \sqrt{\frac{G}{\rho}}$$

where K and G are the bulk modulus and shear modulus of the elastic materials, respectively, Y is the Young's modulus, and v is Poisson's ratio. Note that the speed of longitudinal/compression waves depends both on the compression and shear resistance properties of the material, while the speed of shear waves depends on the shear properties only. Typically, compression waves travel faster in materials than do shear waves.

Isotropic approximations are known for the bulk and shear modulus of silicon. For example, the hydrostatic loads, i.e., bulk modulus is k=97.8 GPa and shear load, twisting a <110> ("X" or "Y") beam, is k=50.9 GPa. The density of silicon as a function of temperature (Density ($\rho$) in gcm-3) is as follows for crystalline silicon:

$\rho=2.33-(2.19/10^5)*T(T=100-1700 K)$

When converted to kg/m$^3$ for use in the speed of sound equation above, $\rho=2330-(2190/10^5)*T$ (T=100–1700 K). Given that this equation is only valid from T=100 to T=1700, then the valid range for $\rho$ is 2328 kg/m$^3$ to 2293 kg/m$^3$. Combining the equations yields a silicon longitudinal velocity for sound as a function of temperature (T) between 100K and 1700K. Note, unlike the equations above, the equations below use B for Bulk Modulus (instead of K) and use K for Kelvin:

$C=((B+4/3*G)/\rho)^{1/2}$ $C(T)=((97.8\ Gpa+4/3*50.9\ Gpa)/(2330-(2190/10^5)*T)kg/m^3)^{1/2}\ m/s$ $C(T)=((97.8*10^9\ pa+4/3*50.9*10^9\ pa)/(2330-(2190/10^5)*T)kg/m^3)^{1/2}\ m/s$ $C(T)=((166*10^9\ pa)/(2330-(2190/10^5)*T)kg/m^3)^{1/2}\ m/s.$ At T=300K (room temperature):

$C(300K)=((166*10^9\ pa)/(2330-(2190/10^5)*300)kg/m^3)^{1/2}\ m/s$ $C(300K)=((166*10^9\ pa)/(2323.43\ kg/m^3))^{1/2}\ m/s$ $C(300K)=8452.58\ m/s=845258\ cm/s$ $1/C=(1.183/10^6)s/cm.$

Given a silicon substrate at a temperature of 300K, it would take a sound wave 1.183 microseconds to propagate a distance of 1 cm between a SAW transmitter and receiver. Conversely, if it takes 1.183 microseconds for a sound wave to travel 1 cm from a SAW transmitter to a receiver (in silicon), then it is possible to calculate the average density ($\rho$) along that path with the following equation:

$1/C=(1.183/10^6)s/cm$ $C=845258\ cm/s=8452.58\ m/s$ $C=((B+4/3*G)/\rho)^{1/2}$ $C^2=(B+4/3*G)/\rho$ $\rho=(B+4/3*G)/C^2.$ Substituting yields:

$\rho=(166*10^9)/(8452.58\ m/s)^2$ $\rho=2323.43\ kg/m^3.$

Since $\rho$ is within a valid range, it is then possible to calculate the average temperature along the path between the SAW transmitter and receiver with the following equation:

$\rho=2330-(2190/10^5)*T$ $T*(2190/10^5)=2330-\rho$ $T=(2330-\rho)/(2190/10^5).$ Substituting yields:

$T=(2330-2323.43)/(2190/10^5)$ $T=6.57/0.0219$ $T=300K.$

If the time it takes for sound to travel the 1 cm from the SAW transmitter to receiver decreases by 100 picoseconds, to a new value of 1.1829 microseconds, then it is possible to first verify the density is within the valid range, and if so, then determine the average temperature along the path between the SAW transmitter and receiver.

$$1/C = (1.1829/10^{\wedge}6)\text{s/cm}$$

$$C = 845380\ \text{cm/s} = 8453.8\ \text{m/s}$$

$$C = ((B + 4/3 * G)/\rho)^{\wedge}\tfrac{1}{2}$$

$$C^{\wedge}2 = (B + 4/3 * G)/\rho$$

$$\rho = (B + 4/3 * G)/C^{\wedge}2.$$

Substituting yields:

$$\rho = (166 * 10^{\wedge}9)/(8453.8\ \text{m/s})^{\wedge}2$$

$$\rho = 2322.76\ \text{kg/m}^{\wedge}3.$$

Since ρ is within the valid range defined, the average temperature along the path between the SAW transmitter and receiver can be calculated with the following equation, $$\rho = 2330 - (2190/10^{\wedge}5) * T$$

$$T * (2190/10^{\wedge}5) = 2330 - \rho$$

$$T = (2330 - \rho)/(2190/10^{\wedge}5).$$

Substituting yields:

$$T = (2330 - 2322.76)/(2190/10^{\wedge}5)$$

$$T = 7.24/0.0219$$

$$T = 330\text{K}.$$

This represents an increase of 30K along the path corresponding to a decrease of 100 picoseconds along the same path.

Figure 7:
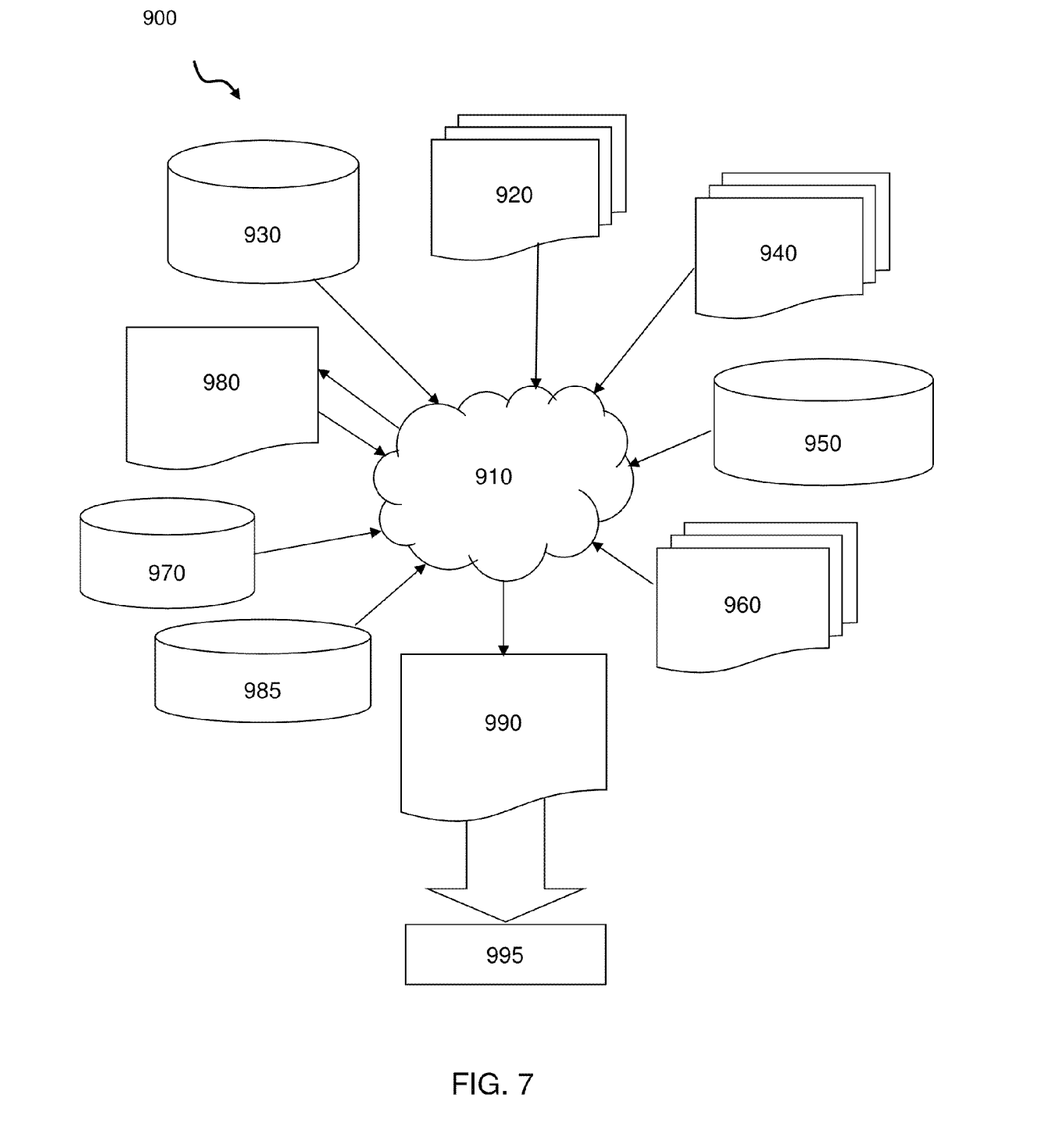
FIG. 7 is a flow diagram of a design process used in semiconductor design, manufacture, and/or test.

FIG. 7 is a flow diagram of a design process used in semiconductor design, manufacture, and/or test. FIG. 7 shows a block diagram of an exemplary design flow 900 used for example, in semiconductor IC logic design, simulation, test, layout, and manufacture. Design flow 900 includes processes, machines and/or mechanisms for processing design structures or devices to generate logically or otherwise functionally equivalent representations of the design structures and/or devices described above and shown in FIGS. 1-5. The design structures processed and/or generated by design flow 900 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 7 illustrates multiple such design structures including an input design structure 920 that is preferably processed by a design process 910. Design structure 920 may be a logical simulation design structure generated and processed by design process 910 to produce a logically equivalent functional representation of a hardware device. Design structure 920 may also or alternatively comprise data and/or program instructions that when processed by design process 910, generate a functional representation of the physical structure of a hardware device. Whether representing functional and/or structural design features, design structure 920 may be generated using electronic computer-aided design (ECAD) such as implemented by a core developer/designer. When encoded on a machine-readable data transmission, gate array, or storage medium, design structure 920 may be accessed and processed by one or more hardware and/or software modules within design process 910 to simulate or otherwise functionally represent an electronic component, circuit, electronic or logic module, apparatus, device, or system such as those shown in FIGS. 1-5. As such, design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 910 preferably employs and incorporates hardware and/or software modules for synthesizing, translating, or otherwise processing a design/simulation functional equivalent of the components, circuits, devices, or logic structures shown in FIGS. 1-5 to generate a netlist 980 which may contain design structures such as design structure 920. Netlist 980 may comprise, for example, compiled or otherwise processed data structures representing a list of wires, discrete components, logic gates, control circuits, I/O devices, models, etc. that describes the connections to other elements and circuits in an integrated circuit design. Netlist 980 may be synthesized using an iterative process in which netlist 980 is resynthesized one or more times depending on design specifications and parameters for the device. As with other design structure types described herein, netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 910 may include hardware and software modules for processing a variety of input data structure types including netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. Design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 910 without deviating from the scope and spirit of the invention. Design process 910 may also include modules for performing standard circuit design processes such as timing analysis, verification, design rule checking, place and route operations, etc.

Design process 910 employs and incorporates logic and physical design tools such as HDL compilers and simulation model build tools to process design structure 920 together with some or all of the depicted supporting data structures along with any additional mechanical design or data (if applicable), to generate a second design structure 990.

Design structure 990 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 920, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1-5. In one embodiment, design structure 990 may comprise a compiled, executable HDL simulation model that functionally simulates the devices shown in FIGS. 1-5.

Design structure 990 may also employ a data format used for the exchange of layout data of integrated circuits and/or symbolic data format (e.g. information stored in a GDSII (GDS2), GL1, OASIS, map files, or any other suitable format for storing such design data structures). Design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1-5. Design structure 990 may then proceed to a stage 995 where, for example, design structure 990: proceeds to tape-out, is released to manufacturing, is released to a mask house, is sent to another design house, is sent back to the customer, etc.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chip comprising:
   at least one transmitter and at least one receiver, the at least one transmitter generating a mechanical wave which is received by the at least one receiver; and
   a timing circuit in communication with the at least one transmitter and the at least one receiver, which measures a time in which the mechanical wave travels between the at least one transmitter and the at least one receiver.

2. The chip of claim 1, wherein the timing circuit is synchronized with the at least one transmitter.

3. The chip of claim 1, wherein the timing circuit triggers the at least one transmitter.

4. The chip of claim 1, wherein the at least one transmitter triggers the timing circuit.

5. The chip of claim 1, wherein the at least one transmitter and the at least one receiver are positioned remotely from an active region of a chip.

6. The chip of claim 1, wherein the least one transmitter and the at least one receiver comprises multiple transmitters and multiple receivers positioned at a periphery of a chip.

7. The chip of claim 1, wherein the at least one transmitter and the at least one receiver are Surface Acoustic Wave (SAW) Microelectromechanical system (MEMS) devices.

8. The chip of claim 1, wherein the at least one transmitter and the at least one receiver are bulk acoustic wave (BAW) devices.

9. The chip of claim 1, wherein the at least one transmitter and the at least one receiver are located on different layers of a 3D integrated circuit, relative to an active region.

10. A structure comprising:
    an active region with at least one device which generates heat;
    at least one transmitter and at least one receiver, the at least one transmitter generating a mechanical wave which is received by the at least one receiver; and
    a timing circuit in communication with the at least one transmitter and the at least one receiver, which measures a time in which the mechanical wave travels between the at least one transmitter and the at least one receiver.

11. The structure of claim 10, wherein the at least one transmitter and the at least one receiver are located on different layers of a 3D integrated circuit, relative to an active region.

12. The structure of claim 10, wherein the at least one transmitter and the at least one receiver are located at a periphery of the chip, remote from an active region.

13. The structure of claim 10, wherein the at least one receiver comprises a plurality of receivers located remotely from the at least one transmitter and remotely from an active region.

14. The structure of claim 10, wherein the at least one transmitter and the at least one receiver are one of SAW MEMS devices fabricated directly on the chip or bulk acoustic wave (BAW) devices.

* * * * *